United States Patent [19]

Michel et al.

[11] Patent Number: 5,767,148
[45] Date of Patent: Jun. 16, 1998

[54] SYNERGISTIC THERAPEUTIC COMPOSITIONS COMPRISING AT LEAST ONE LIGAND SPECIFIC FOR RXRS AT LEAST ONE LIGAND SPECIFIC FOR RAR-α

[75] Inventors: Serge Michel, Roquefort les Pins; Christine Cathelineau; Marie-Cécile Lenoir-Viale, both of Valbonne; Michel Demarchez, Le Bar Sur Loup, all of France

[73] Assignee: Centre International de Recherches Dermatologiques Galderma, Valbonne, France

[21] Appl. No.: 507,913

[22] Filed: Jul. 27, 1995

[30] Foreign Application Priority Data

Jul. 27, 1994 [FR] France .................................. 94 09307

[51] Int. Cl.$^6$ .................... A61K 31/335; A61K 31/195
[52] U.S. Cl. ................................... 514/467; 514/563
[58] Field of Search ............................. 514/467, 563

[56] References Cited

FOREIGN PATENT DOCUMENTS 9303713  3/1993  WIPO .
9321146  10/1993  WIPO .

OTHER PUBLICATIONS

Proc Annu Meet Am Assoc Cancer Res; 33:A565-6 15-07-92. Sporn MB et al, p. 566, col. 1.

Blood, 84 (2) 1994, 446–452. Dawson et al, p. 448, Col. 2, Line 3, p. 450, Col. 2.

Nucleic Acids Res, Mar. 11, 1993, 21 (5), P1231-7, England, Schrader et al.

New Engl. J. Med. 1993, 329/3 (177–189), USA, p. 186, Col. 1, Line 3, Col. 2.

*Primary Examiner*—Jerome D. Goldberg
*Attorney, Agent, or Firm*—Burns, Doane, Swecker & Mathis, L.L.P.

[57] ABSTRACT

Pharmaceutical/dermatological compositions comprising (a) at least one first ligand displaying selective activity for the RXR receptors and (b) at least one second ligand displaying selective activity for the RAR-α receptor, are useful for modulating the proliferation and/or differentiation of HL-60 type cells, in particular for the systemic treatment of acute promyelocytic leukemia.

10 Claims, 4 Drawing Sheets

SYNERGISTIC THERAPEUTIC COMPOSITIONS COMPRISING AT LEAST ONE LIGAND SPECIFIC FOR RXRS AT LEAST ONE LIGAND SPECIFIC FOR RAR-α

BACKGROUND OF THE INVENTION

1. Technical Field of the Invention

The present invention relates to novel pharmaceutical compositions comprising synergistic admixtures of at least one ligand displaying selective activity for RXR type nuclear receptors and at least one ligand displaying selective activity for RAR-α type nuclear receptors, and to the use of said novel compositions as modulators of the proliferation and/or differentiation of a particular cell type (HL-60 cells), especially for the systemic treatment of acute promyelocytic leukemia.

2. Description of the Prior Art

Retinoic acid is a known potent modulator (i.e., an inhibitor or, to the contrary, a stimulator, depending on the nature of the cells treated) of the differentiation and proliferation of many normal or transformed cell types. For example, it inhibits the differentiation of epithelial cells such as the keratinocytes of the epidermis. It also inhibits the proliferation of many transformed cells such as melanoma cells. These effects on proliferation and differentiation can affect the same cell type simultaneously, as is, for example, the case with the human promyelocytic cells designated HL-60; thus, it too is known to this art that the proliferation of these cells is inhibited by retinoic acid and, at the same time, that their differentiation into granulocytes is enhanced.

The above HL-60 cells are especially advantageous and important, principally in light of the fact that they are analogous to the promyelocytic cells of patients suffering from acute promyelocytic leukemia. These patients are at present treated with retinoic acid, this treatment eliciting, at least initially, a significant remission of the disease. However, the phenomenon of resistance or habituation with regard to retinoic acid has been observed in patients thus treated, which ultimately impairs the efficacy of the therapy.

It is also known that, in general, all-trans-retinoic acid acts on the differentiation and proliferation of cells by interacting with nuclear receptors or RARs (retinoic acid receptors) contained in the cell nucleus. Three identified subtypes of RAR receptors exist at present, designated, respectively, RAR-α, RAR-β and RAR-γ. These receptors, after binding of the ligand (i.e., retinoic acid), interact with the promoter region of genes regulated by retionic acid at specific response elements. To bind to the response elements, the RARs heterodimerize with another type of receptor known as RXR. The natural ligand of the RXRs is 9-cis-retinoic acid. As for all-trans-retinoic acid, it is known that 9-cis-retinoic acid is capable, on the one hand, of inhibiting the proliferation of the above-mentioned HL-60 cells, and, on the other, of stimulating their differentiation into granulocytes. The RXRs are considered to be "master regulatory proteins" since they interact with other members of the steroid receptor superfamily such as the vitamin $D_3$ receptor (VDR) or the triiodothyroxine receptor (TR). Furthermore, the RXRs can interact with specific response elements in the form of homodimers.

Many synthetic structural analogs of retinoic acid or of 9-cis-retinoic acid, commonly termed "retinoids," have to date been described in the literature. Certain of these molecules are capable of binding and specifically activating RARs or, to the contrary, RXRs. Furthermore, certain analogs may bind and activate one particular subtype of RAR receptor (α, β or γ). Other analogs, lastly, do not display any particular selective activity with respect to these different receptors. In this respect, for example, 9-cis-retinoic acid activates both RARs and RXRs, without significant selectivity for one or the other of these receptors (nonspecific ligand), whereas all-trans-retinoic acid, in its turn, selectively activates RARs (RAR-specific ligand), without discrimination between subtypes. In general and qualitatively, a given substance (or ligand) is termed selective with respect to a given family of receptors (or with respect to a particular receptor of this family) when said substance displays a strong affinity for all of the receptors of this family (or, respectively, for the particular receptor of this family) and when it displays, moreover, a low affinity for all of the receptors of any other family (or, respectively, for all other receptors, of this same family or otherwise). Quantitatively, the affinity is measured by means of classical binding techniques (Kd values), and it is generally accepted that any species which, with regard to a given first receptor, possesses a Kd at least 10-fold less, and preferably at least 15-fold less, than the Kd it possesses with regard to a given second receptor may be qualified as a selective substance with respect to this first receptor relative to this second receptor. The evaluation of the selective or non-selective character of a given substance with regard to a given receptor is traditionally carried out by means of in vitro biological tests per se known to this art, as indicated below.

SUMMARY OF THE INVENTION

It has now unexpectedly been determined that particular therapeutic admixtures comprising (a) a retinoid specific for one particular receptor subtype, namely, an RAR-α receptor and (b) a retinoid specific for RXRs, enable the proliferation on the one hand (which is in this instance inhibited) and the differentiation on the other (which is in this instance enhanced) of the HL-60 cells described above to be modulated most exceptionally.

This is all the more surprising by reason of the fact that a substance specific for RXRs, when it is used alone, displays no or substantially no activity with respect to these same cells, and that a retinoid specific for RARs (without discrimination between subtypes) is also inactive, again when it is used alone. Moreover, the combination of a retinoid specific for RAR-β or for RAR-γ with a retinoid specific for RXRs does not, in its turn, exhibit any activity.

DETAILED DESCRIPTION OF BEST MODE AND PREFERRED EMBODIMENTS OF THE INVENTION

Figure 1:
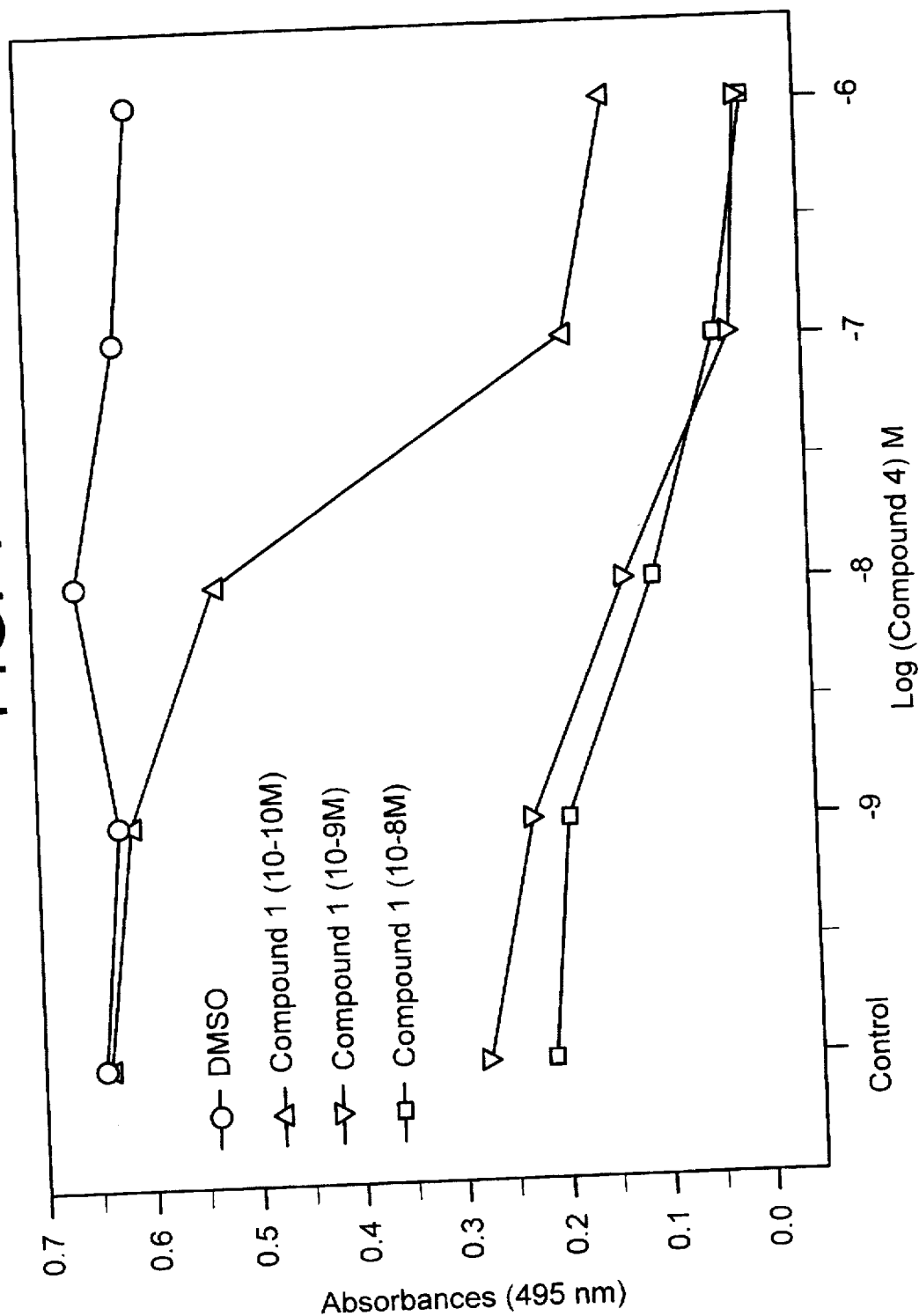
FIG. 1 is a graph illustrating the effect of combinatory admixture of a Compound 1 specific for RAR-α with a Compound 4 specific for RXRs on the proliferation of HL-60 cells.
Figure 2:
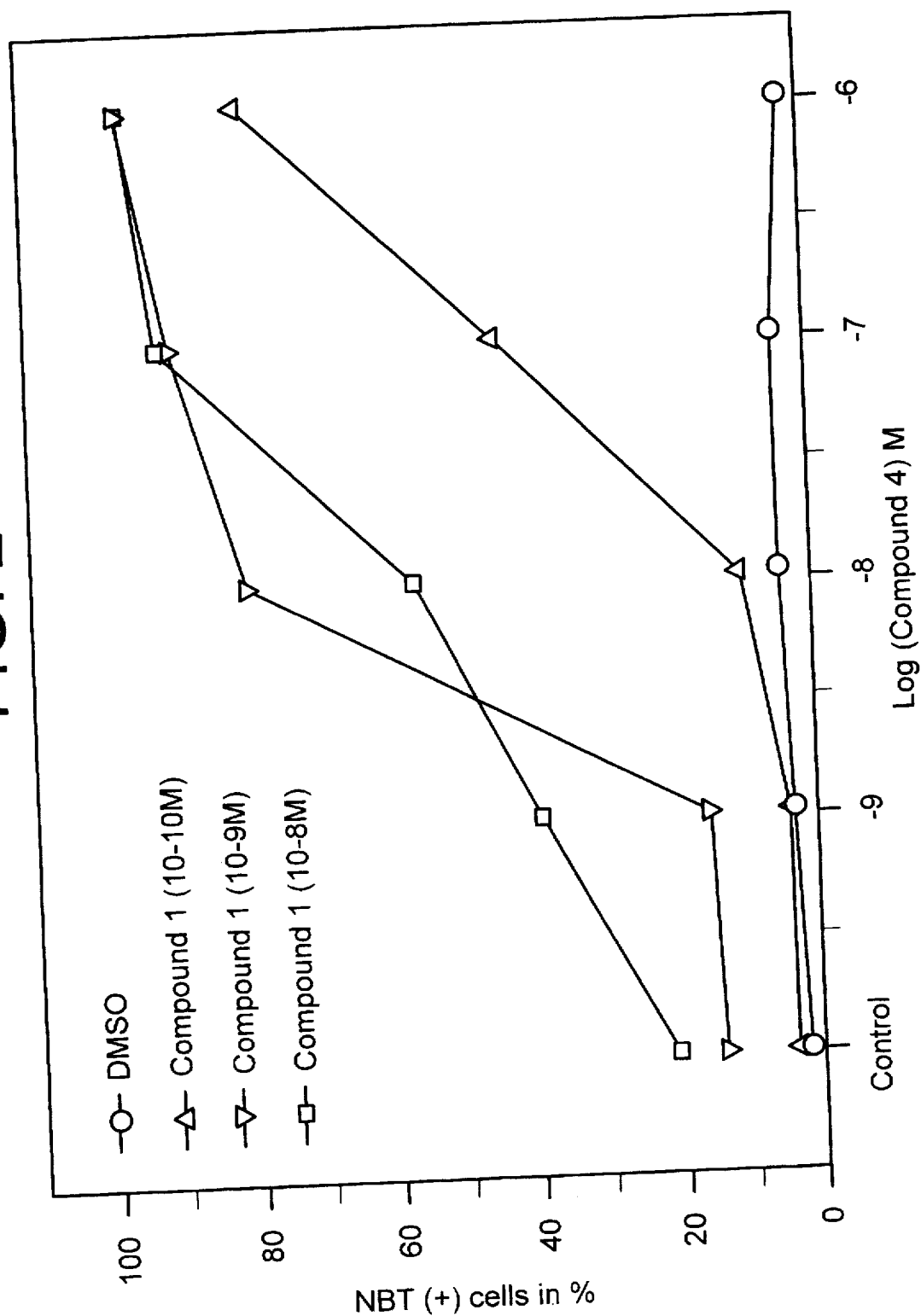
FIG. 2 is a graph illustrating the effect of combinatory admixture of Compound 1 specific for RAR-α with Compound 4 specific for RXRs on the differentiation of HL-60 cells.

More particularly according to the present invention, combinatory immixture of a retinoid specific for RAR-α with a retinoid specific for RXRs, in light of the exceptional activities which it elicits in respect of HL-60 cells, has now been found to be especially advantageous for the systemic therapeutic treatment of patients suffering from acute promyelocytic leukemia.

Thus, in one aspect thereof, the present invention features novel medicinal compositions comprising, in a physiologically or pharmaceutically acceptable vehicle, diluent, or carrier, at least one first ligand displaying selective activity for the RXR receptors and at least one second ligand displaying selective activity for the RAR-α receptor.

This invention also features such pharmaceutical and/or dermatological compositions (medicinal products) for modulating the proliferation and/or differentiation of an HL-60 type cell system, in particular for the systemic treatment of acute promyelocytic leukemia.

In general, it should be appreciated that the active or effective doses to elicit the desired therapeutic effect always remain very low, which presents a considerable advantage when need exists to combat problems of tolerance or undesirable side effects which are liable to arise in the individuals to be treated or over the course of treatment.

In the description that follows, by "topical route" is intended any technique or mode of administration of a product by direct application of same to a superficial (or external) part of the body, such as the skin. By "systemic route" is intended any technique or mode of administration of a product by a route other than topical, for example oral and/or parenteral.

The novel pharmaceutical or medicinal compositions of the invention, well suited, in particular, for the therapeutic treatment of the disorder indicated above, comprise, in a physiologically or pharmaceutically acceptable vehicle, carrier or diluent compatible with the mode of administration adopted therefor, at least one first ligand displaying selective activity for the RXR receptors and at least one second ligand displaying selective activity for the RAR-α receptor, as active principles. It is of course possible to employ one or more ligands displaying specific activity with respect to the RXR receptors in admixture with one or more ligands displaying specific activity with respect to the RAR-α receptor.

The administration of the compositions according to the invention is advantageously carried out via the enteral, parenteral, topical or ocular route. However, preferably, the subject compositions are packaged in a form suitable for systemic application.

For enteral administration, the medicinal products can be in the form of tablets, hard gelatin capsules, dragées, syrups, suspensions, solutions, powders, granules, emulsions, microspheres or nanospheres, or lipid or polymeric vesicles permitting a controlled release. For parenteral administration, the compositions can be in the form of solutions or suspensions for perfusion or for injection.

The mixtures of biologically active agents according to the invention are typically administered at daily dosages of approximately 0.01 mg/kg to 100 mg/kg body weight, in from 1 to 3 doses/day.

For topical administration, the pharmaceutical compositions, which are hence more especially intended for the treatment of the skin or the mucosae, can be in the form of ointments, creams, milks, salves, powders, impregnated pads, solutions, gels, sprays, lotions or suspensions. They can also be in the form of lipid or polymeric microspheres or nanospheres or vesicles, or of polymeric patches and of hydrogels permitting a controlled release of the active agents. These compositions for topical administration can, moreover, be either in anhydrous form or in an aqueous form, according to the clinical indication.

The compositions for topical use according to the invention contain the retinoid or retinoids specific for RXRs at a concentration generally ranging from 0.001% to 10% by weight, and preferably from 0.1% to 1% by weight, relative to the total weight of the composition. The retinoid and retinoids specific for RAR-α are typically present at a concentration generally ranging from 0.001% to 10% by weight, and preferably from 0.1% to 1% by weight, relative to the total weight of the composition.

For ocular administration, the compounds are principally eye lotions.

The medicinal or pharmaceutical compositions according to the invention can of course contain, in addition, inert or even pharmacodynamically active additives and adjuvants, or combinations of such additives and adjuvants, and in particular: wetting agents; depigmenting agents such as hydroquinone, azelaic acid, caffeic acid or kojic acid; emollients; hydrating agents such as glycerol, PEG 400, thiamorpholinone and derivatives thereof or, alternatively, urea; antiseborrhoeic or anti-acne agents such as S-carboxymethylcysteine, S-benzylcysteamine, or salts or derivatives thereof, or benzoyl peroxide; antifungal agents such as ketoconazole or 4,5-polymethylene-3-isothiazolidones; antibacterials, carotenoids, and in particular β-carotene; antipsoriatic agents such as anthralin and derivatives thereof; and, lastly, 5,8,11,14-eicosatetraynoic and 5,8,11-eicosatriynoic acids, or the esters and amides thereof.

The compositions according to the invention can also contain flavor improvers, preservatives such as para-hydroxybenzoic acid esters, stabilizing agents, moisture regulating agents, pH regulating agents, osmotic pressure modifying agents, emulsifying agents, UV-A and UV-B screening agents, and antioxidants such as α-tocopherol, butylated hydroxyanisole or butylated hydroxytoluene.

As indicated above, the selective or non-selective nature of a given molecular species with respect to one or more given nuclear receptors can be determined by means of tests which are standard in this art. These tests are described, in particular, in the following references: (1) "Selective Synthetic Ligands for Nuclear Retinoic Acid Receptor Subtypes" in *RETINOIDS*, Progress in Research and Clinical Applications, Chapter 19 (pp. 261–267), Marcel Dekker Inc., edited by Maria A. Livrea and Lester Packer; (2) "Synthetic Retinoids: Receptor Selectivity and Biological Activity" in *Pharmacol Skin*, Basel, Karger, 1993, Volume 5, pp. 117–127; (3) "Selective Synthetic Ligands for Human Nuclear Retinoic Acid Receptors" in *Skin Pharmacology*, 1992, Vol. 5, pp. 57–65; (4) "Identification of Synthetic Retinoids with Selectivity for Human Nuclear Retinoic Acid Receptor-γ" in *Biochemical and Biophysical Research Communications*, Vol. 186, No. 2, July 1992, pp. 977–983; (5) "Selective High Affinity RAR-α or RAR-β Retinoic Acid Receptor Ligands" in *Mol. Pharmacol.*, Vol. 40, pp. 556–562.

Particularly exemplary retinoids selective for RAR-α according to the present invention include the folowing:

(i) 4-[(5,6,7,8-tetrahydro-5,5,8,8-tetramethyl-2-naphthyl) carboxamido]benzoic acid (Compound 1, employed in the examples below);

(ii) 4-[(5,6,7,8-tetrahydro-5,5,8,8-tetramethyl-2-naphthyl)carbamoyl]benzoic acid (Compound 2).

And particularly exemplary retinoids selective for RXRs according to the invention include the following:

(i) 4-[(5,6,7,8-tetrahydro-5,5,8,8-tetramethyl-2-naphthyl) carbonyl]benzoic acid ethylene acetal (Compound 4, employed in the examples below);

(ii) (E)-2-[2-(3,5,5,8,8-pentamethyl-5,6,7,7-tetrahydro-2-naphthyl)-1-propenyl]-4-thiophenecarboxylic acid (Compound 5);

(iii) 4-[(3,5,5,8,8-pentamethyl-5,6,7,8-tetrahydro-2-naphthyl)carbonyl]benzoic acid (Compound 6).

As indicated above, the compositions according to the invention are advantageously used for modulating in vitro and/or in vivo the proliferation and/or differentiation of HL-60 type cell systems. These cells have been described, in particular, in the following publications: (1) "Induction of Differentiation of the Human Promyelocytic Leukemia Cell Line (HL-60) by Retinoic Acid" in *Proc. Natl. Acad. Sci. USA*, 77, pp. 2936–2940, and (2) "Human Leukemic Models of Myelomonocytic Development: a review of the HL-60 and U937 cell lines" in *J. Leucocyte Biology*, 37, pp. 407–422; they are, in addition, available in the form of cultures from the European Collection of Animal Cell Cultures, Division of Biologics, Porton Down, Salisbury SP4 OJ4, England.

Even more specifically, the compositions according to the invention are useful for the in vivo and/or in vitro treatment of mammalian organisms suffering from acute promyelocytic leukemia.

In order to further illustrate the present invention and the advantages thereof, the following specific examples are given, it being understood that same are intended only as illustrative and in nowise limitative.

EXAMPLE 1

This example demonstrates the in vitro activity of the synergistic combinations according to the invention with respect to the proliferation and/or differentiation of HL-60 cells.

The HL-60 cells used were cells which were obtained directly from the European Collection of Animal Cell Cultures, identified above.

The experimental protocol and the methods of determination of the activities (proliferation, differentiation) were the following:

Cell culture:

The cells were cultured at 37° C. in a humid atmosphere in the presence of 5% $CO_2$ in RPMI 1640 medium (Gibco) with the addition of glutamine (40 mM) and of 10% (v/v) of fetal calf serum (FCS).

Treatment of cells:

HL-60 cells were inoculated in the proportion of $4 \times 10^5$ cells in 2 ml of medium into RPMI 1640 medium (Gibco) with the addition of Hepes buffer pH 7.3 (10 mM), glutamine (40 mM), transferrin (5 mg/ml), insulin (5 mg/ml), selenium (5 ng/ml) and 2% (v/v) of FCS in 10 $cm^2$ cluster wells. The cells were treated immediately following inoculation with the retinoids (Compounds 1, 3 or 4 as described above) diluted in DMSO. The final DMSO concentration in the culture medium did not exceed 0.2% (v/v). After 4 days of culture, the cells were harvested to determine proliferation and differentiation.

Measurement of proliferation:

Cell proliferation was determined by means of an apparatus designated "Cell proliferation kit II" (XTT assay) employed according to the directions of the manufacturer (Boehringer, ref. 1465 05). It is expressed in absorbence units at 495 nm. The lower the measured absorbence, the more inhibited the proliferation of HL-60 cells.

Measurement of differentiation:

The differentiation of HL-60 cells into granulocytes or monocytes was measured with the NET (nitro blue tetrazolium) test (T. R. Breitman, Growth and differentiation of human myeloid leukaemia cell line HL-60 in: *Methods in Enzymology*, vol. 190, pp. 118–130, (ed. L. Packer) Academic Press Inc. New York (1990)). This test enabled the number of differentiated cells relative to the total number of cells to be determined.

All the results obtained are shown in FIGS. 1 to 4. These figures quantify changes in the degree of inhibition of proliferation of HL-60 cells, or the changes in the level of differentiated HL-60 cells, as a function of the active agents used on the one hand and of their concentrations on the other. The values given at the control point correspond to the results obtained when no RXR-specific retinoid was employed; on the other hand, the DMSO curve (-0-) corresponds to the results obtained when only an RXR-specific retinoid was employed as the active agent.

Figure 3:
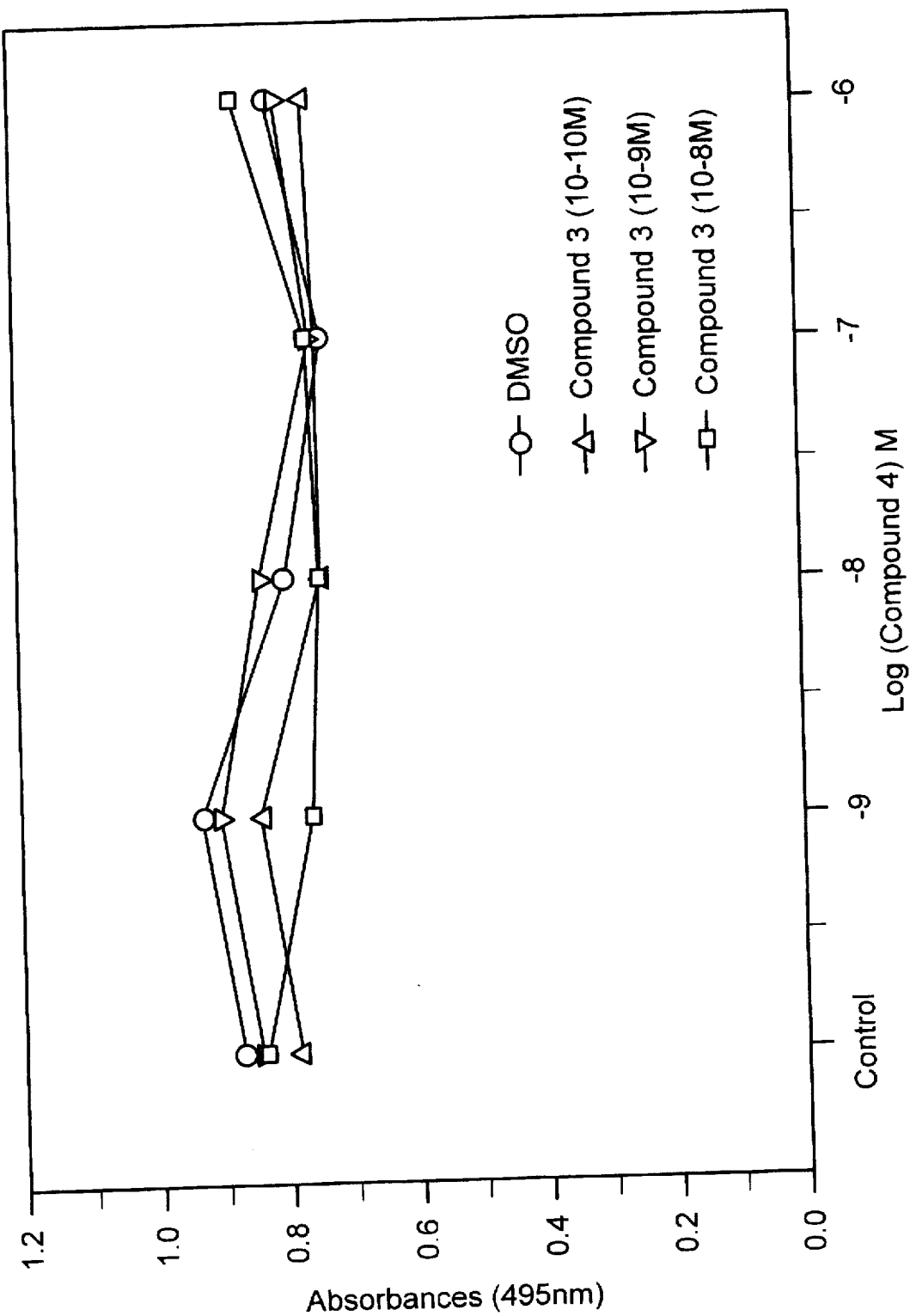
FIG. 3 is a graph illustrating the effect of combinatory admixture of a Compound 3, namely, 6-[3-(1-adamantyl)-4-hydroxyphenyl]-2-naphthoic acid, specific for RAR-α with Compound 4 specific for RXRs on the proliferation of HL-60 cells.
Figure 4:
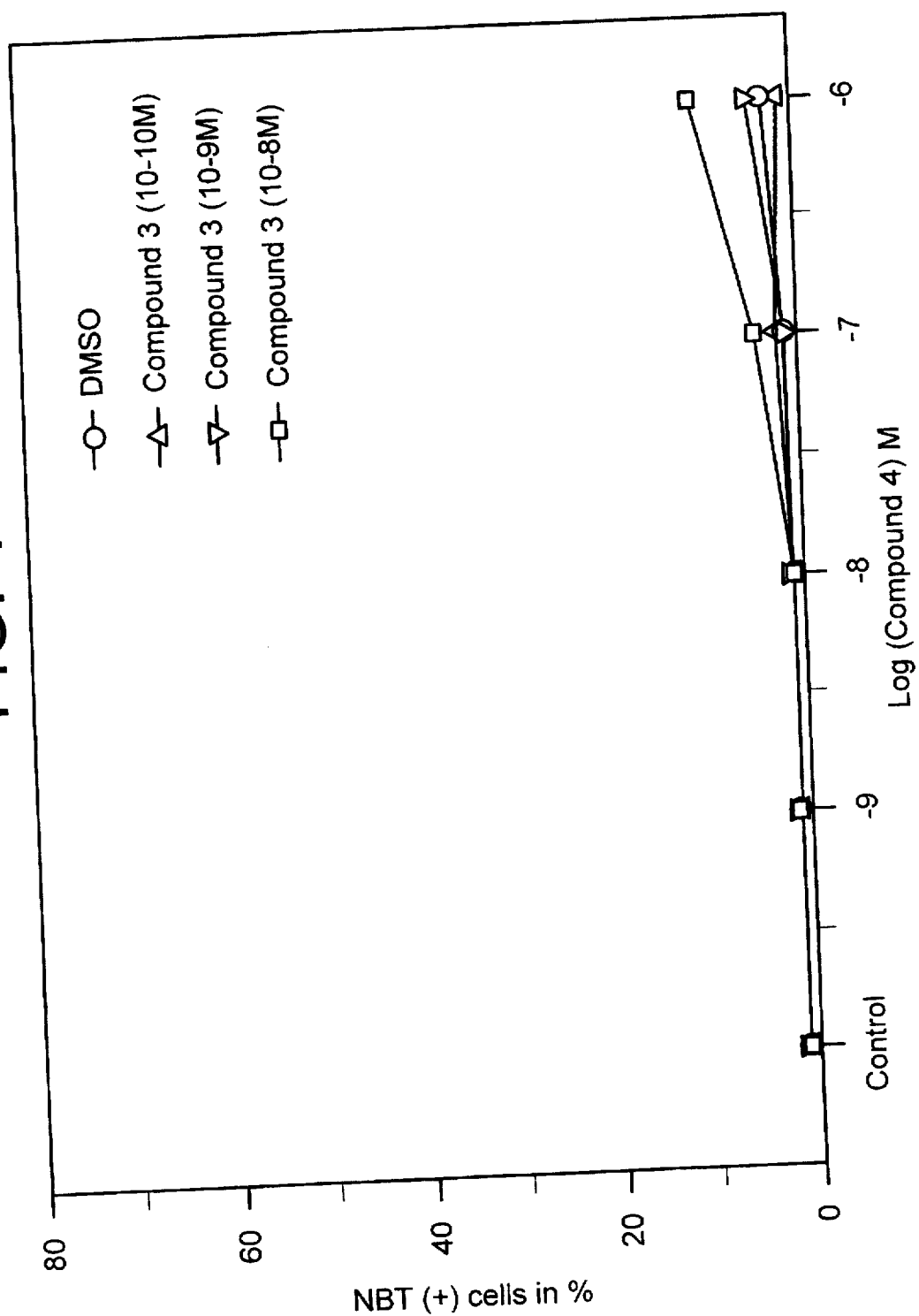
FIG. 4 is a graph illustrating the effect of combinatory admixture of Compound 3 specific for RAR-α with Compound 4 specific for RXRs on the different of HL-60 cells.

These figures show clearly that the combination of an RAR-α-specific retinoid (Compound 1) and a retinoid specific for RXRs (Compound 4) displayed very good activity with respect to the proliferation and differentiation of HL-60 cells (see FIGS. 1 and 2), whereas the combination of a retinoid specific for RAR-γ (Compound 3) with this same retinoid specific for RARs exhibited no activity (see FIGS. 3 and 4).

EXAMPLE 2

In this example, various specific formulations based on the combinations according to the invention are illustrated (the Compounds 1 and 4 are those described above):

(A) ORAL ROUTE:

(1) 0.2 g Tablet:

| | |
|---|---|
| (a) Compound 1 | 0.001 g |
| (b) Compound 4 | 0.001 g |
| (c) Starch | 0.113 g |
| (d) Dicalcium phosphate | 0.020 g |
| (e) Silica | 0.020 g |
| (f) Lactose | 0.030 g |
| (g) Talc | 0.010 g |
| (h) Magnesium stearate | 0.005 g |

(2) Suspension for oral use, in 10 ml ampoules:

| | |
|---|---|
| (a) Compound 1 | 0.05 g |
| (b) Compound 4 | 0.05 g |
| (c) Glycerol | 1.000 g |
| (d) Sorbitol, 70% | 1.000 g |
| (e) Saccharin sodium | 0.010 g |
| (f) Methyl para-hydroxybenzoate | 0.080 g |
| (g) Flavoring qs | |
| (h) Purified water qs | 10 ml |

(B) TOPICAL ROUTE:

(1) Ointment:

| | |
|---|---|
| (a) Compound 1 | 0.1 g |
| (b) Compound 4 | 0.1 g |
| (c) Isopropyl myristate | 81.520 g |
| (d) Light liquid paraffin | 9.100 g |
| (e) Silica ("Aerosil 200" marketed by DEGUSSA) | 9.180 g |

(2) Nonionic water-in-oil cream:

| | |
|---|---|
| (a) Compound 1 | 0.100 g |
| (b) Compound 4 | 0.100 g |

-continued

| | |
|---|---|
| (c) Mixture of emulsive lanolin alcohols, of waxes and of oils ("Eucerin anhydrous" marketed by BDF) | 39.900 g |
| (d) Methyl para-hydroxybenzoate | 0.075 g |
| (e) Propyl para-hydroxybenzoate | 0.075 g |
| (f) Sterile demineralized water qs | 100 g |
| (3) Lotion: | |
| (a) Compound 1 | 0.100 g |
| (b) Compound 4 | 0.100 g |
| (c) Polyethylene glycol (PEG 400) | 69.800 g |
| (d) Ethanol, 95% | 30.000 g |
| (4) Hydrophobic ointment: | |
| (a) Compound 1 | 0.300 g |
| (b) Compound 4 | 0.300 g |
| (c) Isopropyl myristate | 36.400 g |
| (d) Silicone oil ("Rhodorsil 47 V 300" marketed by RHONE-POULENC) | 36.400 g |
| (e) Beeswax | 13.600 g |
| (f) Silicone oil ("Abil 300,000 cst" marketed by GOLDSCHMIDT) qs | 100 g |
| (5) Nonionic oil-in-water cream: | |
| (a) Compound 1 | 0.500 g |
| (b) Compound 4 | 0.500 g |
| (c) Cetyl alcohol | 4.000 g |
| (d) Glyceryl monostearate | 2.500 g |
| (e) PEG 50 stearate | 2.500 g |
| (f) Shea butter | 9.200 g |
| (g) Propylene glycol | 2.000 g |
| (h) Methyl para-hydroxybenzoate | 0.075 g |
| (i) Propyl para-hydroxybenzoate | 0.075 g |
| (j) Sterile demineralized water qs | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter comprising a synergistic therapeutically effective amounts of at least one first ligand displaying selective activity for the RXR receptors and at least one second ligand displaying selective activity for the RAR-α receptor, wherein the first ligand is 4-[(5,6,7,8-tetrahydro-5,5,8,8-tetramethyl-2-naphthyl)carbonyl] benzoic acid ethylene acetal and the second ligand is 4-[(5,6,7,8-tetrahydro-5,5,8,8-tetramethyl-2-naphthyl) carboxamido]benzoic acid.

2. The composition of matter as defined by claim 1, further comprising a pharmaceutically/physiologically acceptable vehicle, carrier or diluent therefor.

3. The composition of matter as defined by claim 2, adapted for systemic administration to a mammalian organism.

4. The composition of matter as defined by claim 2, adapted for topical administration to a mammalian organism.

5. The composition of matter as defined by claim 2, comprising from 0.001% to 10% by weight of said (a) at least one first ligand.

6. The composition of matter as defined by claim 5, comprising from 0.1% to 1% by weight of said (a) at least one first ligand.

7. The composition of matter as defined by claim 5, comprising from 0.001% to 10% by weight of said (b) at least one second ligand.

8. The composition of matter as defined by claim 7, comprising from 0.1% to 1% by weight of said (b) at least one second ligand.

9. The composition of matter as defined by claim 1, comprising a tablet, gelatin capsule, dragée, syrup, suspension, solution, powder, granules, emulsion, microspheres or nanospheres, lipid or polymeric vesicles, ointment, cream, milk, gel, salve, impregnated pad, spray, lotion, patch, or hydrogel.

10. A regimen for the treatment of acute promyelocytic leukemia in a mammalian organism in need of such treatment, comprising systemically administering thereto a therapeutically effective amount of the composition of matter as defined by claim 1.

* * * * *

UNITED STATES PATENT AND TRADEMARK OFFICE
CERTIFICATE OF CORRECTION

PATENT NO. : 5,767,148
DATED : June 16, 1998
INVENTOR(S) : Serge Michel et al.

It is certified that error appears in the above-identified patent and that said Letters Patent is hereby corrected as shown below:

At Column 2, line 61, please change "different" to --differentiation--.

At Column 6, line 29, please change "RARs" to --RXRs--.

Signed and Sealed this

Twenty-second Day of December, 1998

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,767,148
DATED : June 16, 1998
INVENTOR(S) : Serge Michel et al.

It is certified that error appears in the above-indentified patent and that said Letters Patent is hereby corrected as shown below:

At Column 1, line 48, please change "retionic" to --retinoic--.

At Column 2, line 56, please change "RAR-α" to --RAR-γ--.

At Column 2, line 60, please change "RAR-α" to --RAR-γ--.

Signed and Sealed this

Twelfth Day of January, 1999

Attest:

*Attesting Officer*

*Acting Commissioner of Patents and Trademarks*